US010357372B2

United States Patent
Brownhill et al.

(10) Patent No.: US 10,357,372 B2
(45) Date of Patent: Jul. 23, 2019

(54) RADIAL HEAD TRIALS

(71) Applicant: Mayo Foundation for Medical Education and Research, Rochester, MN (US)

(72) Inventors: James Brownhill, Orlando, FL (US); Andrew Rynearson, Rochester, MN (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 0 days.

(21) Appl. No.: 14/779,872

(22) PCT Filed: Mar. 28, 2014

(86) PCT No.: PCT/US2014/032151
§ 371 (c)(1),
(2) Date: Sep. 24, 2015

(87) PCT Pub. No.: WO2014/160924
PCT Pub. Date: Oct. 2, 2014

(65) Prior Publication Data
US 2016/0051365 A1     Feb. 25, 2016

Related U.S. Application Data

(60) Provisional application No. 61/806,315, filed on Mar. 28, 2013.

(51) Int. Cl.
*A61F 2/30*          (2006.01)
*A61F 2/38*          (2006.01)
(Continued)

(52) U.S. Cl.
CPC .. *A61F 2/3804* (2013.01); *A61B 2017/00707* (2013.01); *A61F 2/4684* (2013.01);
(Continued)

(58) Field of Classification Search
CPC .. A61F 2002/30329; A61F 2002/30393; A61F 2002/30428; A61F 2002/30331;
(Continued)

(56) References Cited

U.S. PATENT DOCUMENTS 4,242,758 A    1/1981   Amis et al.
4,383,337 A    5/1983   Volz et al.
(Continued)

FOREIGN PATENT DOCUMENTS

EP       0624352 B1    10/1997
EP       1080701 B1    8/2006
(Continued)

OTHER PUBLICATIONS

"U.S. Appl. No. 13/827,985, Final Office Action dated Dec. 15, 2014", 6 pgs.
(Continued)

*Primary Examiner* — Thomas Sweet
*Assistant Examiner* — Melissa A Hoban
(74) *Attorney, Agent, or Firm* — Schwegman Lundberg & Woessner, P.A.

(57) ABSTRACT

A radial head trial device for replacement of a proximal radial head includes a stem component having a center longitudinal axis extending between a proximal end and a distal end, a head component axially and removably attachable to the stem component, wherein the head component is interchangeable with a selection of other head components each axially and removably attachable to the stem component, an anti-rotation feature, and a recess, wherein the anti-rotation feature is structured to be received in the recess to prohibit rotation of the head component relative to the stem component.

13 Claims, 8 Drawing Sheets

(51) Int. Cl.
*A61B 17/00* (2006.01)
*A61F 2/46* (2006.01)

(52) U.S. Cl.
CPC .............. *A61F 2002/30367* (2013.01); *A61F 2002/3827* (2013.01)

(58) Field of Classification Search
CPC ...... A61F 2002/5803; A61F 2220/0025; A61F 2220/0033; A61F 2230/0006
See application file for complete search history.

(56) References Cited

U.S. PATENT DOCUMENTS

| | | | |
|---|---|---|---|
| 5,879,395 A | | 3/1999 | Tornier et al. |
| 5,935,172 A | * | 8/1999 | Ochoa ..................... A61L 27/58 606/77 |
| 6,217,616 B1 | | 4/2001 | Ogilvie |
| 6,270,529 B1 | | 8/2001 | Terrill-Grisoni et al. |
| 6,361,563 B2 | | 3/2002 | Terrill-Grisoni et al. |
| 6,656,225 B2 | | 12/2003 | Martin |
| 6,709,459 B1 | | 3/2004 | Cooney, III et al. |
| 6,767,368 B2 | | 7/2004 | Tornier |
| 7,160,329 B2 | | 1/2007 | Cooney, III et al. |
| 7,608,110 B2 | | 10/2009 | O'driscoll et al. |
| 7,641,695 B2 | | 1/2010 | Guederian |
| 7,708,781 B2 | | 5/2010 | Scheker |
| 7,740,661 B2 | | 6/2010 | Baratz et al. |
| 7,951,198 B2 | * | 5/2011 | Sucec .................. A61B 17/562 606/300 |
| 8,034,116 B2 | | 10/2011 | Vander Meulen et al. |
| 8,048,162 B2 | | 11/2011 | Scheker et al. |
| 8,110,005 B2 | | 2/2012 | Berelsman et al. |
| 8,114,163 B2 | | 2/2012 | Berelsman et al. |
| 8,366,781 B2 | | 2/2013 | Berelsman et al. |
| 8,377,066 B2 | | 2/2013 | Katrana et al. |
| 9,901,452 B2 | | 2/2018 | Brownhill |
| 2004/0186580 A1 | * | 9/2004 | Steinmann ............. A61B 17/15 623/20.11 |
| 2004/0225367 A1 | | 11/2004 | Glien et al. |
| 2005/0075735 A1 | | 4/2005 | Berelsman et al. |
| 2005/0216090 A1 | * | 9/2005 | O'Driscoll ............ A61F 2/3804 623/20.32 |
| 2005/0246032 A1 | | 11/2005 | Bokros et al. |
| 2006/0052725 A1 | | 3/2006 | Santilli |
| 2008/0288079 A1 | | 11/2008 | Leibel |
| 2009/0240336 A1 | * | 9/2009 | Vander Meulen .... A61F 2/3804 623/18.11 |
| 2009/0281631 A1 | * | 11/2009 | Naidu ................... A61F 2/3804 623/20.11 |
| 2010/0030339 A1 | | 2/2010 | Berelsman et al. |
| 2010/0121390 A1 | | 5/2010 | Kleinman |
| 2010/0241236 A1 | | 9/2010 | Katrana et al. |
| 2010/0262252 A1 | | 10/2010 | Berelsman et al. |
| 2010/0312349 A1 | | 12/2010 | Berelsman et al. |
| 2011/0029089 A1 | | 2/2011 | Giuliani et al. |
| 2011/0112649 A1 | | 5/2011 | Isch et al. |
| 2011/0125276 A1 | | 5/2011 | Berelsman et al. |
| 2011/0144759 A1 | | 6/2011 | Berelsman et al. |
| 2011/0172781 A1 | | 7/2011 | Katrana et al. |
| 2012/0083892 A1 | | 4/2012 | Kehres et al. |
| 2012/0109323 A1 | | 5/2012 | Berelsman et al. |
| 2014/0012388 A1 | | 1/2014 | Brownhill et al. |
| 2014/0074246 A1 | * | 3/2014 | Huebner ............... A61F 2/3804 623/20.11 |
| 2014/0277524 A1 | | 9/2014 | Brownhill |
| 2018/0133017 A1 | | 5/2018 | Brownhill |

FOREIGN PATENT DOCUMENTS

| | | |
|---|---|---|
| EP | 1772118 B1 | 6/2009 |
| EP | 2078511 B1 | 10/2010 |
| EP | 2561833 A1 | 2/2013 |
| EP | 2978388 B1 | 4/2018 |
| FR | 2923154 A1 | 5/2009 |
| WO | WO-0013617 A1 | 3/2000 |
| WO | WO-2004000174 A1 | 12/2003 |
| WO | WO-2005086939 A2 | 9/2005 |
| WO | WO-2006060322 A1 | 6/2006 |
| WO | WO-2010098791 A2 | 9/2010 |
| WO | WO-2011017620 A2 | 2/2011 |
| WO | WO-2014159203 A1 | 10/2014 |
| WO | WO-2014160924 A1 | 10/2014 |

OTHER PUBLICATIONS

"U.S. Appl. No. 13/827,985, Non Final Office Action dated Apr. 29, 2015", 8 pgs.
"U.S. Appl. No. 13/827,985, Non Final Office Action dated Jul. 8, 2014", 6 pgs.
"U.S. Appl. No. 13/827,985, Response filed Mar. 16, 2015 to Final Office Action dated Dec. 15, 2014", 14 pgs.
"U.S. Appl. No. 13/827,985, Response filed Nov. 6, 2014 to Non-Final Office Action dated Jul. 8, 2014", 15 pgs.
"International Application Serial No. PCT/US2014/022495, International Search Report dated Jun. 25, 2014", 4 pgs.
"International Application Serial No. PCT/US2014/022495, Written Opinion dated Jun. 25, 2014", 6 pgs.
"International Application Serial No. PCT/US2014/032151, International Search Report dated Jul. 2, 2014", 3 pgs.
"International Application Serial No. PCT/US2014/032151, Written Opinion dated Jul. 2, 2014", 6 pgs.
Wikipedia.org—pear (fruit), (Dec. 11, 2015), 9 pgs.
"U.S. Appl. No. 13/827,985, Advisory Action dated Mar. 2, 2016", 3 pgs.
"U.S. Appl. No. 13/827,985, Advisory Action dated Mar. 7, 2017", 3 pgs.
"U.S. Appl. No. 13/827,985, Examiner Interview Summary dated Mar. 2, 2017", 3 pgs.
"U.S. Appl. No. 13/827,985, Examiner Interview Summary dated Oct. 8, 2014", 3 pgs.
"U.S. Appl. No. 13/827,985, Final Office Action dated Feb. 3, 2017", 7 pgs.
"U.S. Appl. No. 13/827,985, Final Office Action dated Dec. 17, 2015", 7 pgs.
"U.S. Appl. No. 13/827,985, Non Final Office Action dated Jun. 30, 2016", 7 pgs.
"U.S. Appl. No. 13/827,985, Response filed Feb. 17, 2016 to Final Office Action dated Dec. 17, 2015", 14 pgs.
"U.S. Appl. No. 13/827,985, Response filed Feb. 24, 2017 to Final Office Action dated Feb. 3, 2017", 11 pgs.
"U.S. Appl. No. 13/827,985, Response filed May 3, 2017 to Advisory Action dated Mar. 7, 2017", 12 pgs.
"U.S. Appl. No. 13/827,985, Response filed May 17, 2016 to Advisory Action dated Mar. 2, 2016", 18 pgs.
"U.S. Appl. No. 13/827,985, Response filed Oct. 27, 2015 to Non Final Office Action dated Apr. 29, 2015", 16 pgs.
"U.S. Appl. No. 13/827,985, Response filed Oct. 31, 2016 to Non Final Office Action dated Jun. 30, 2016", 13 pgs.
"Application Serial No. PCT/US2014/032151, International Preliminary Report on Patentability dated Oct. 8, 2015", 8 pgs.
"European Application Serial No. 14717907.1, Response filed May 16, 2016 to Communication pursuant to Rules 161(1) and 162 EPC dated Nov. 5, 2015", 10 pgs.
"European Application Serial No. 14719503.6, Communication Pursuant to Article 94(3) EPC dated Nov. 29, 2016", 4 pgs.
"European Application Serial No. 14719503.6, Response filed Apr. 11, 2017 to Communication Pursuant to Article 94(3) EPC dated Nov. 29, 2016", 12 pgs.
"European Application Serial No. 14719503.6, Response filed Jun. 23, 2016 to Communication pursuant to Rules 161(1) and 162 EPC dated Dec. 2, 2015", 11 pgs.
"International Application Serial No. PCT/US2014/022495, International Preliminary Report on Patentability dated Sep. 24, 2015", 8 pgs.
"U.S. Appl. No. 13/827,985, Non Final Office Action dated May 19, 2017", 6 pgs.

(56) References Cited

OTHER PUBLICATIONS

"U.S. Appl. No. 13/827,985, Notice of Allowance dated Oct. 13, 2017", 7 pgs.
"U.S. Appl. No. 13/827,985, Response filed Jul. 26, 2017 to Non Final Office Action dated May 19, 2017", 15 pgs.
"U.S. Appl. No. 13/827,985, Notice of Allowability dated Dec. 6, 2017", 2 pgs.
"European Application Serial No. 14717907.1, Communication Pursuant to Article 94(3) EPC dated Feb. 7, 2018", 5 pgs.
"European Application Serial No. 14717907.1, Response filed Jun. 18, 2018 to Communication Pursuant to Article 94(3) EPC dated Feb. 7, 2018", 9 pgs.
"European Application Serial No. 18168423.4, Extended European Search Report dated Apr. 17, 2019", 8 pgs.

\* cited by examiner

RADIAL HEAD TRIALS

CLAIM OF PRIORITY

This application is a U.S. National Stage Filing under 35 U.S.C. 371 from International Application No. PCT/US2014/032151, filed on 28 Mar. 2014, and published as WO2014/160924 on 2 Oct. 2014, which claims the benefit of U.S. Provisional Patent Application Ser. No. 61/806,315, filed on Mar. 28, 2013, the benefit of priority of each of which are claimed hereby, and which are incorporated by reference herein in their entirety.

BACKGROUND AND SUMMARY

The present disclosure is directed toward implants, implant trials, instrumentation and methods for joint arthroplasty. The embodiments disclosed may be used in a radial head replacement procedure.

In radial head replacement procedures, a radial head prosthesis is implanted into the intramedullary canal of the proximal radius. Determining the proper size of radial head prosthesis is important so that an optimal fit between the radius, humerus and ulna, including other prosthetic components, can be attained.

The present disclosure includes radial head trialing devices which include a stem component, and variously sized and shaped head components, each connectable to the stem component. The connection may be a snap-fit, non-rotatable connection. In a method of use, the stem component may be placed in the intramedullary canal of a resected radius. The various trial head components may be interchangeably attached to the stem component in situ to determine selection of an optimally sized and shaped radial head prosthesis. An instrument to facilitate removal of the trial head components is disclosed.

This disclosure is related to U.S. patent application Ser. No. 13/827,985 entitled Radial Head Implant, which is incorporated by reference herein in its entirety.

LIST OF FIGURES

Figure 1:
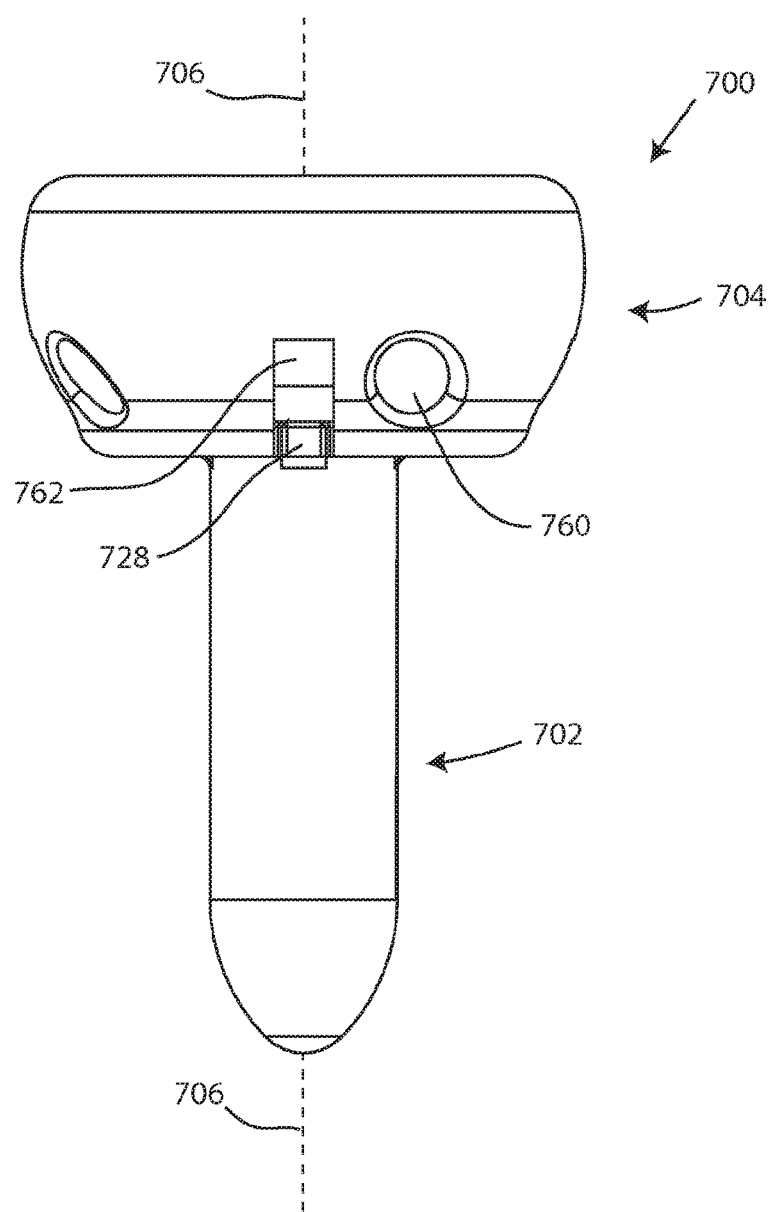
FIG. 1 is a side view of an embodiment of a radial head trial device including a trial head component, and a stem component.
Figure 5A:
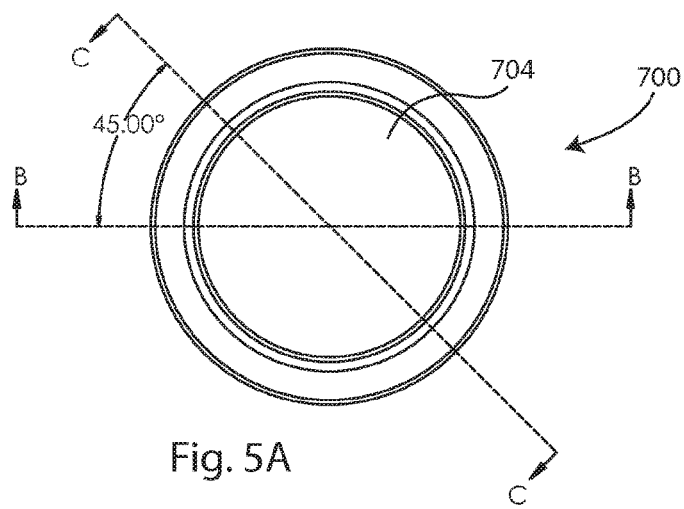
Figure 5B:
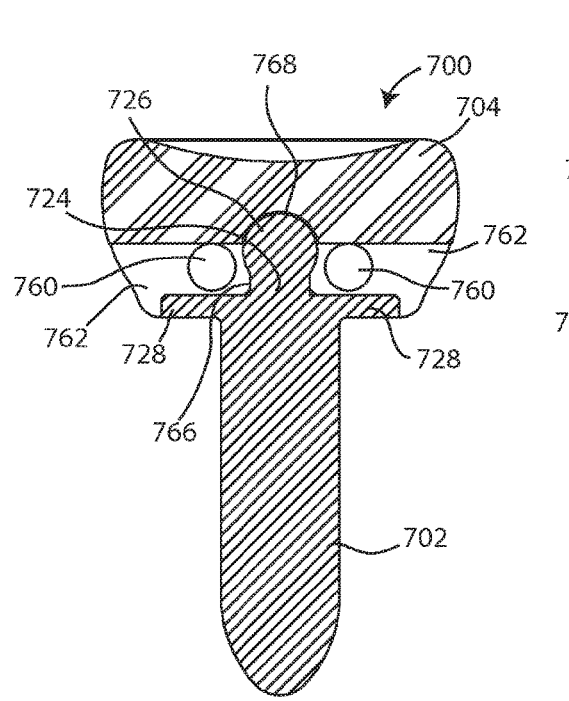
Figure 5C:
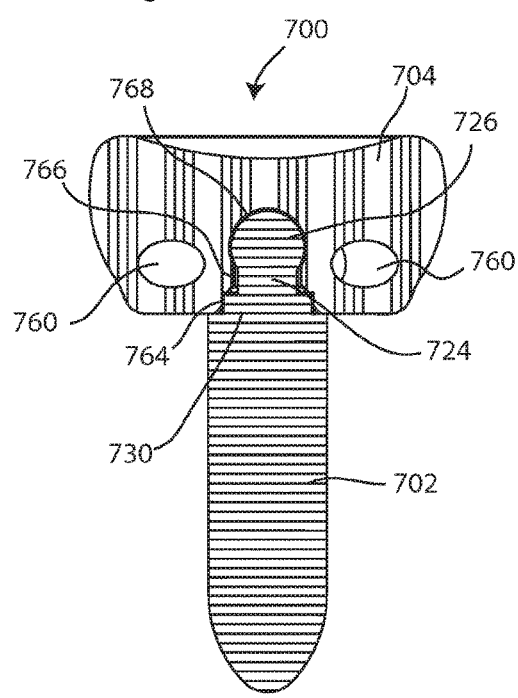
Figures 6A, 6B:
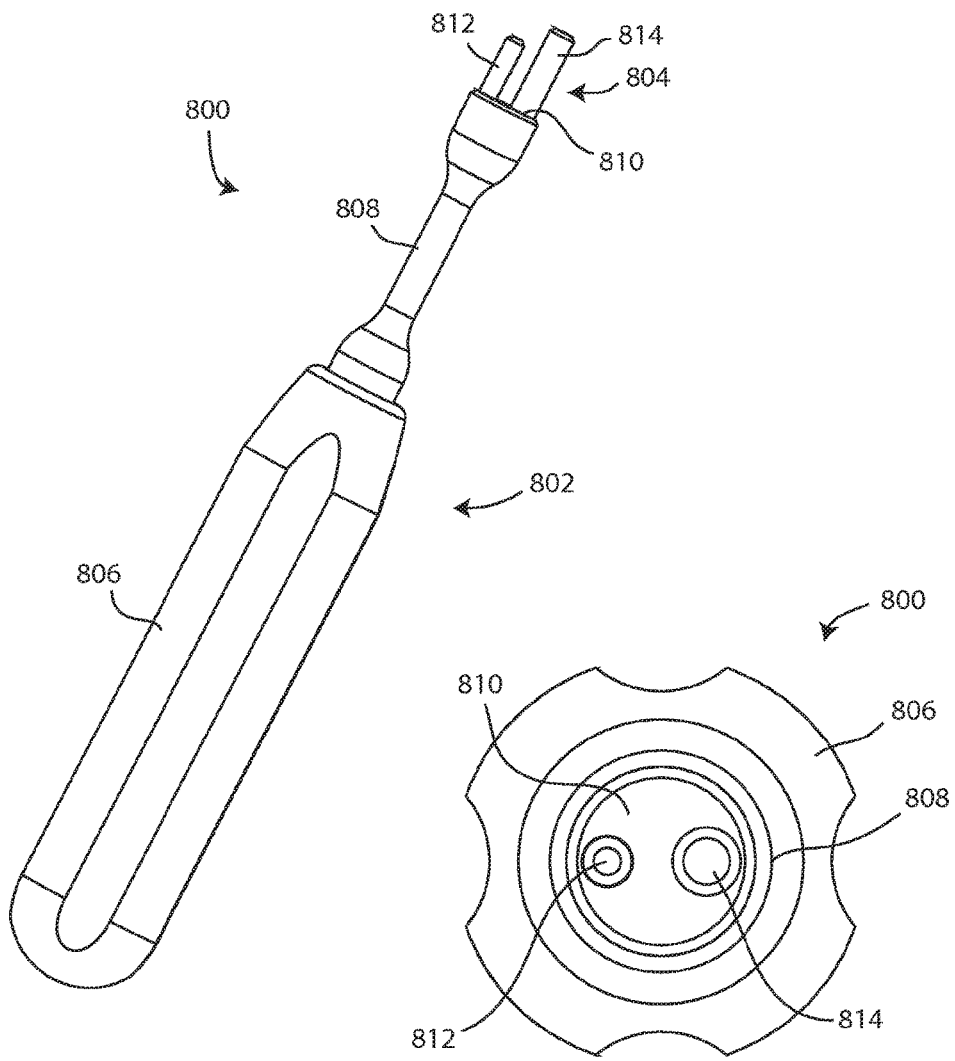
Figure 7A:
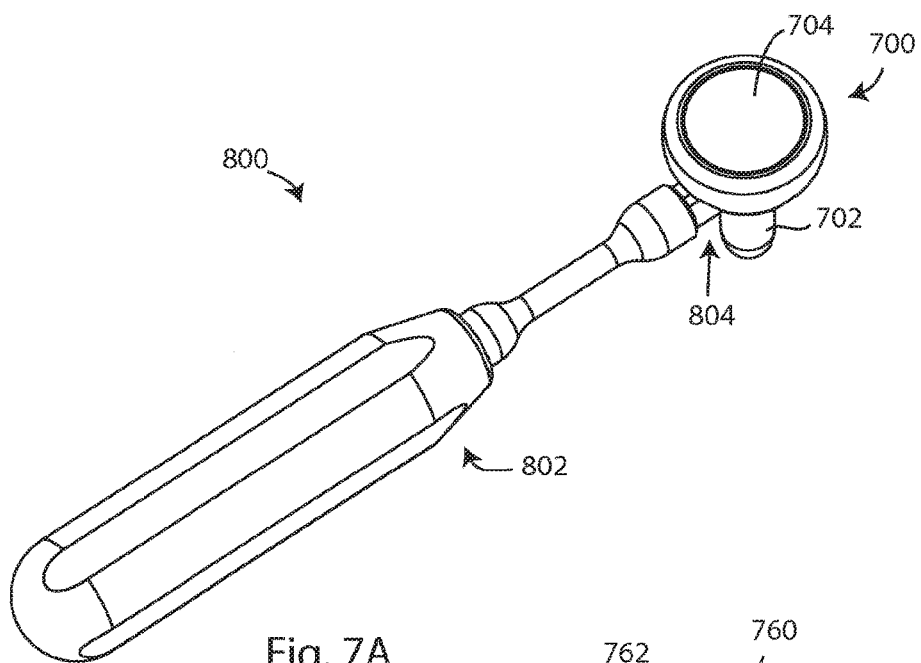
Figure 7B:
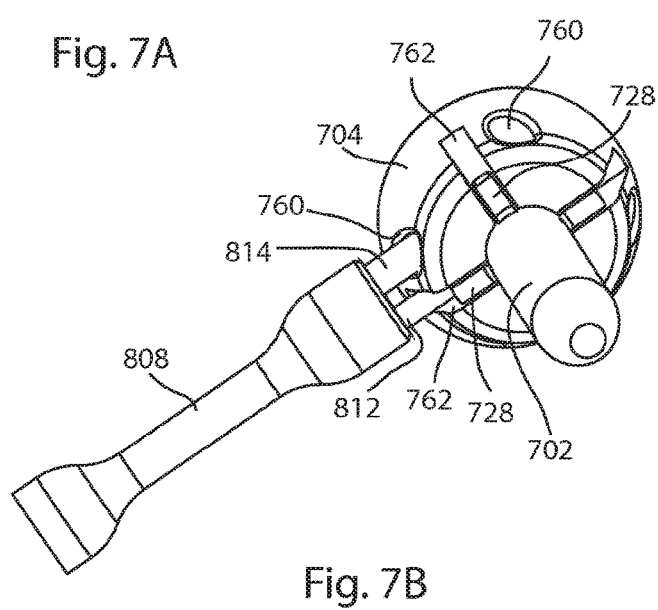

FIG. 5A is a top view of the radial head trial device of FIG. 1; FIG. 5B is a cross-sectional view of the radial head trial device of FIG. 1, taken along line B-B of FIG. 5A; FIG. 5C is another cross-sectional view of the head component of the radial head trial device of FIG. 1, taken along line C-C of FIG. 5A;

FIG. 6A is a perspective view of an instrument configured to engage with the radial head trial of FIG. 1; FIG. 6B is a top view of the instrument of FIG. 6A; and FIG. 7A is a perspective view of the instrument of FIG. 6A engaged with the radial head trial of FIG. 1; FIG. 7B is a bottom perspective view of a portion of the instrument of FIG. 6A engaged with the radial head trial of FIG. 1.

BRIEF DESCRIPTION

In this specification, standard medical directional terms are employed with their ordinary and customary meanings. Superior means toward the head. Inferior means away from the head. Anterior means toward the front. Posterior means toward the back. Medial means toward the midline, or plane of bilateral symmetry, of the body. Lateral means away from the midline of the body. Proximal means toward the trunk of the body. Distal means away from the trunk. In the context of a human arm, distal means toward the hand, and proximal means toward the shoulder.

In this specification, a standard system of three mutually perpendicular reference planes is employed. A sagittal plane divides a body into bilaterally symmetric right and left portions. A coronal plane divides a body into anterior and posterior portions. A transverse plane divides a body into superior and inferior portions.

Referring to FIGS. 1-5C, a radial head trial device 700 includes a stem component 702, and a cap or head component 704. The stem component 702 and head component 704 may be radially symmetrical about a center longitudinal axis 706 defined by the center of the stem component. The head component 704 is removable from the stem component 702, and may be replaced by other head components of varying sizes and shapes.

Figure 2:
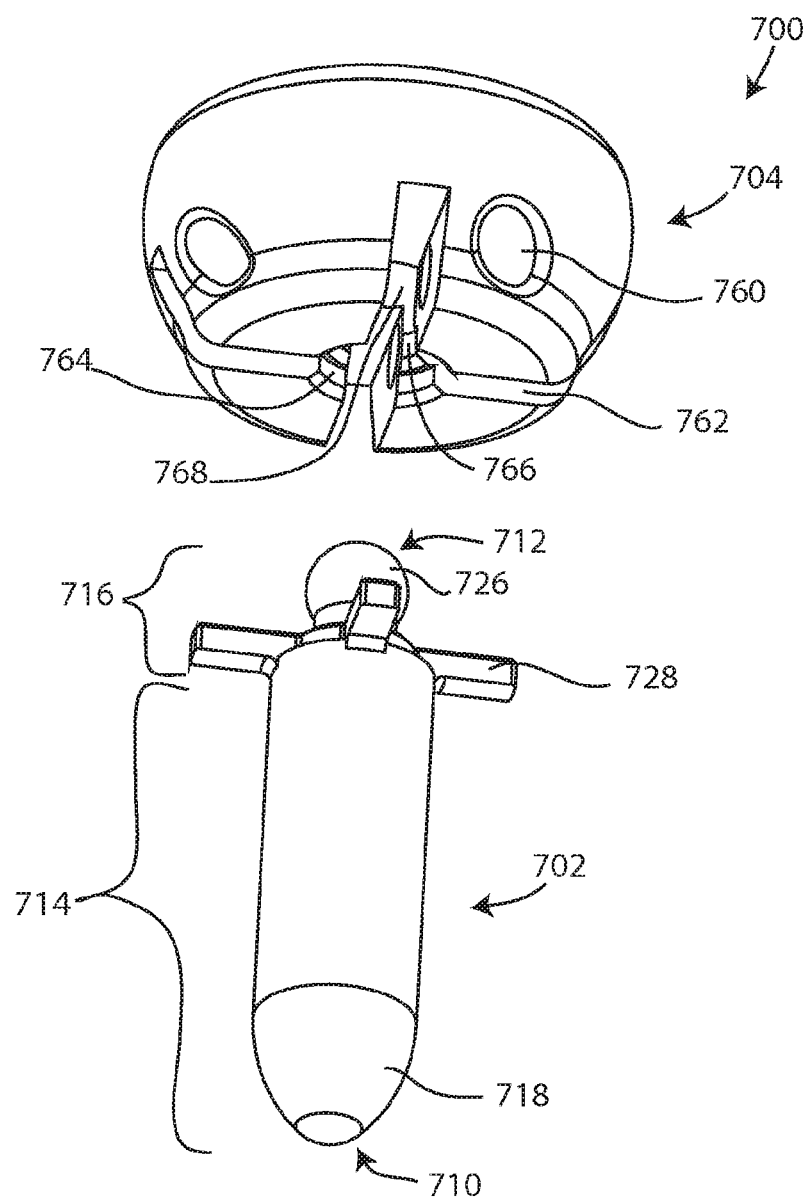
FIG. 2 is an isometric exploded view of the radial head trial device of FIG. 1.
Figures 3A, 3B:
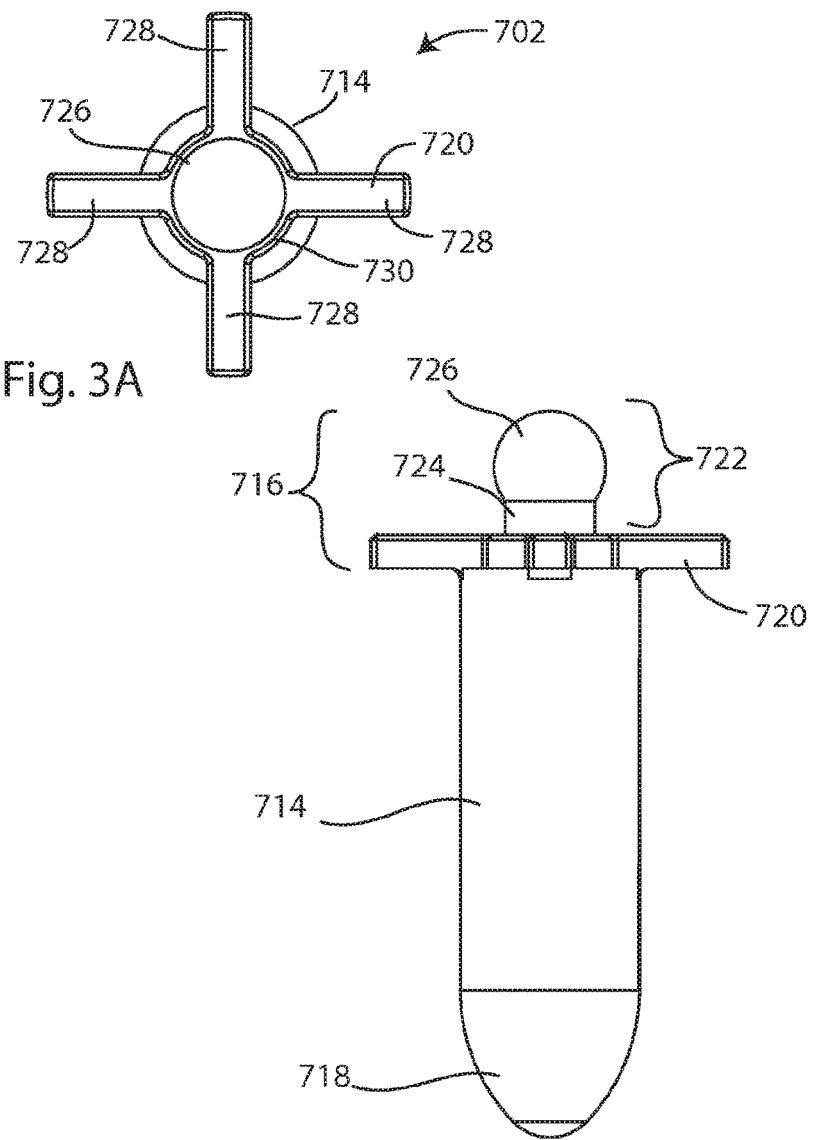
FIG. 3A is a top view of the stem component of the radial head trial device of FIG. 1.
FIG. 3B is a side view of the stem component of the radial head trial device of FIG. 1.

Referring to FIGS. 2-3B, the stem component 702 has a distal end 710 and a proximal end 712. The stem component includes a stem shaft portion 714 and a stem attachment portion 716. The stem shaft portion 714 is generally cylindrical, which may allow easy insertion, rotation and removal of the stem component in the intramedullary canal. A tip 718 of the shaft portion 714 may be rounded or tapered; in the embodiment shown it is bullet-shaped. A variety of different diameter and/or length stem components 702 may be provided. However, the dimensions of the stem attachment portion 716 may be standardized so that any head component can be attached to any stem component, regardless of the dimensions of the shaft portion 714.

The stem attachment portion 716 includes a base structure 720 and a boss structure 722. The boss structure 722 may further include a neck portion 724, which may be cylindrical, and a spherical portion 726. The base structure 720 is intermediate between the stem shaft portion 714 and the boss structure 722, and the boss structure 722 protrudes proximally from the base structure 720. In the embodiment shown, the base structure 720 is shaped as a plus sign, with four arms 728, each arm extending orthogonally from the center axis 706, each arm 728 being 90° from its neighboring arms. The arms 728 project medial-laterally past the outer diameter of the stem shaft portion 714. The boss structure 722 may have a smaller outer diameter than the outer diameter of the stem shaft portion 714. A base ring 730 extends between and connects the arms 728. The arms 728 serve as angular and rotational stabilizers when the head component 704 is attached to the stem component 702, preventing rotation of the head component 704 relative to the stem component 702 once they are properly attached to one another. In other embodiments, other anti-rotation features to prevent rotation between the head and the stem are contemplated, including one or more arms, pegs, posts, fins, flanges, dovetails or other external or internal anti-rotation features known in the art. These features may be in the plus-shaped or cruciform arrangement as shown, or may be in another arrangement. The length, width and/or depth of the arms 728 or other anti-rotation features may vary.

Referring to FIGS. 4A-4D, the head component 704 includes a proximal, or first end 740 and a distal, or second end 742. A peripheral wall 744 extends between and connects the first and second ends 740, 742. The first end 740 includes a circular rim 746 which encircles a concave portion 748. There is a smooth transition between the rim 746 and the concave portion 748. A first bearing surface 750 is formed on the first end 740, and may bear against a distal humerus or humeral implant during a trialing process. A second bearing surface 752 is on the exterior or the peripheral wall 744, and may bear against a proximal ulna or ulnar implant during the trialing process. In the embodiment shown, the peripheral wall 744 and second bearing surface 752 are annular but non-cylindrical, having no constant radius from the central longitudinal axis 706. A proximal to distal profile 754 of the second bearing surface 752, seen for example in FIG. 4A, as the sides of the head 704 between the first end 740 and the second end 742, is formed of a contiguous series of arcs, with no intervening straight portions. The proximal to distal profile includes at least one convexly curved section 756, which may be centered on the axis 706 so as to form a spherical portion of the head, and a concavely curved section 758. The concave section 758 allows easier insertion of the head component 704 into the proximal radius by reducing engagement with the distal humerus during implantation. The peripheral wall and the second bearing surface may be described as circumferential, as they encircle the head 704 between the first end 740 and the second end 742. In another embodiment, the head component 704 may have straight sides, and the peripheral wall and second bearing surface are cylindrical.

A plurality of bores 760 extend transversely into the head component 704. In the embodiment shown, four bores 760 are evenly arrayed about the head component and open out through the peripheral wall 744. The bores 760 are sized and shaped to engage with a connection feature on an instrument 800. Other embodiments may have more or fewer bores, no bores, or other features for engagement with an instrument. In the embodiment shown, bores 760 are blind and terminate within the head component 704; in other embodiments they may extend through the head component and open out on an opposite aspect.

Figure 4A:
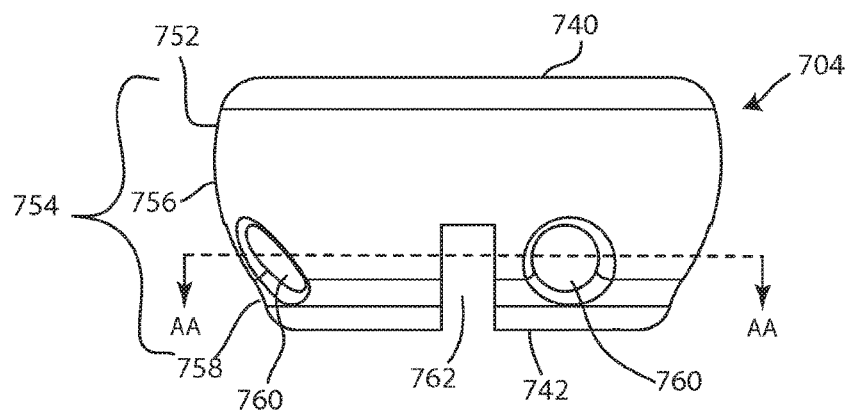
FIG. 4A is a side view of the head component of the radial head trial device of FIG. 1.
Figure 4B:
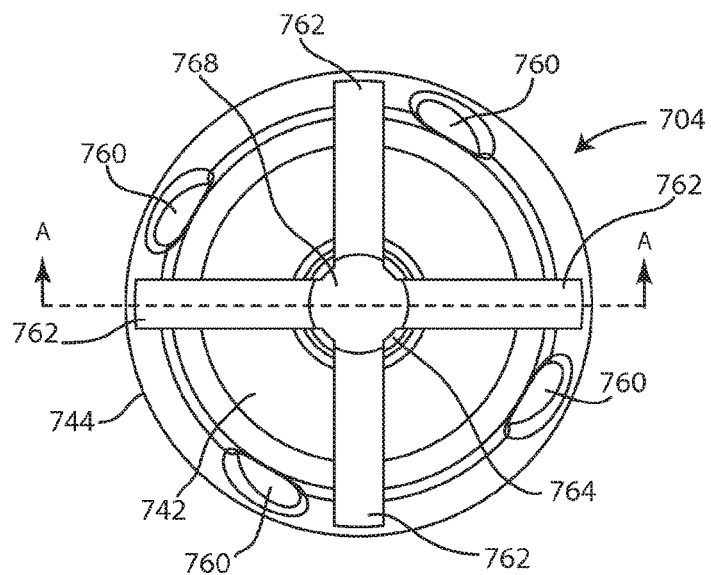
FIG. 4B is a bottom view of the head component of the radial head trial device of FIG. 1.
Figure 4C:
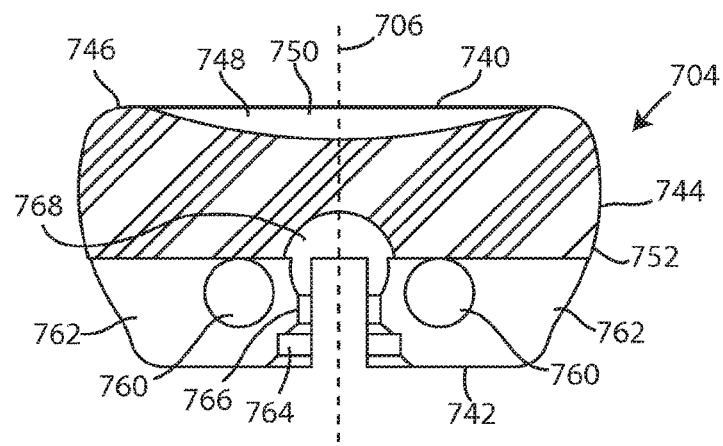
FIG. 4C is a cross-sectional view of the head component of the radial head trial device of FIG. 1, taken along line A-A of FIG. 4B.
Figure 4D:
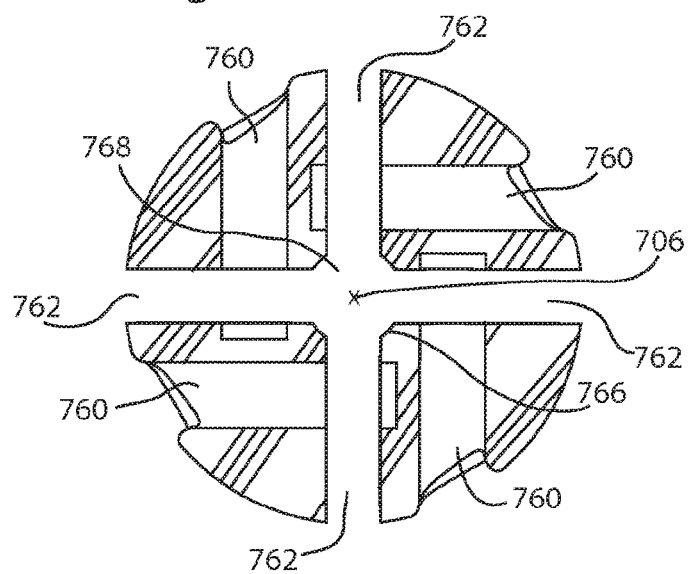
FIG. 4D is another cross-sectional view of the head component of the radial head trial device of FIG. 1, taken along line AA-AA of FIG. 4A.

At the distal end 742 of the head component 704, four cutouts, or slots 762 are arranged in a plus sign pattern, complementary to the arms 728 on the stem component 702. The slots 762 are each recessed into the distal end 742. Each slot 762 extends orthogonally from the center axis 706, each slot 762 being 90° from its neighboring arms. The slots 762 serve to relieve stress as the head component 704 is attached and detached from the stem component 702. In other embodiments there may be more or fewer slots, to complement the number of arms or other anti-rotation features on the stem component 704. It is also appreciated that in other embodiments the locations of the arms 728 and slots 762 may be reversed; for example the stem component may include slots or other recesses to receive arms, or other anti-rotation features, formed on the head component. Referring to FIG. 4D, each bore 760 may intersect and/or cross a slot 762. Each bore 760 is also parallel to at least one slot 762, and perpendicular to at least one other slot 762.

The head component 704 further includes attachment features to accommodate the base ring 730 and boss structure 722 of the stem component. A recessed ring 764 interconnects the slots 762, and is shaped to receive the base ring 730. An annular shoulder 766, which may be cylindrical, is proximal to the slots 762 and base ring 730, and is shaped to receive the neck portion 724 of the boss structure 722. The annular shoulder 766 forms a press fit zone for retention of the spherical portion 726 of the head component. A spherical recess 768 is proximal to the shoulder 766, and is shaped to receive the spherical portion 726 of the boss structure 722. The slots 762 extend through the annular shoulder 766, allowing deflection of the annular shoulder 766 as the spherical portion 726 is moved through the annular shoulder 766. It is appreciated that a continuous opening is formed from the distal end 742 through the recessed ring 764, past the annular shoulder 766, and into the spherical recess 768. The connection between the head component 704 and the stem component 702 may be described as a snap fitting or a press fitting.

In a method of use, a radius is proximally resected to expose the intramedullary canal. Trial stem component 702 is inserted with shaft portion 714 extending distally into the intramedullary canal. A trial head component 704 is selected, and connected to the trial stem component in situ. The head component 704 is attached axially onto the stem component 702. As the head component 704 is attached, the spherical portion 726 of the boss structure 722 is pressed through the annular shoulder 766. The slots 762 on the head component 704 relieve the stress of the pressing force from the spherical portion 726 of the stem component 702 through the press fit zone of the head component. Once the spherical portion 726 of the trial stem 702 has passed through the annular shoulder 766 it enters the spherical recess 768 of the trial radial head, where it will be in clearance with shoulder 766 encircling neck portion 724 to retain the spherical portion 726 within the spherical recess 768. As the spherical portion is received in the spherical recess, the arms 728 are received in the slots 762 and the base ring 730 is received in the recessed ring 764. The engagement of the arms 728 in the slots 762 prevents rotation of the head component 704 relative to the stem component 702, and limits angular movement of the head component. The connection between the head component 704 and the stem component 702 may be described as a snap fitting or a press fitting. The process allows for a secure lock between the radial head trial and stem which will maintain its position during trialing. As seen in FIG. 5B, the arms 728 are distal to the bores 760, allowing room in the slots 762 for insertion of instrument 800.

An alternative embodiment of the trial radial head prosthesis may not include the anti-rotation features such as arms 728 and slots 762, but may still include the snap fitting between the head component 704 and the stem component 704. This embodiment allows for interchangeable trial head components of varying dimensions, while allowing rotation and/or angulation between the head component 704 and the stem component 702. Thus this embodiment would be useful in a trialing process for a bipolar radial head prosthesis.

Another alternative embodiment of the trial radial head prosthesis may include a taper fit between the head component 704 and the stem component 702. In this embodiment, a fork-shaped instrument may be used to disengage the head component from the stem component for interchanging of trial head components.

Referring to FIGS. 6A-7B, an instrument 800, which may be described as a removal instrument, is engageable with trial head component 704 to remove the trial head component 704 from locking connection with trial stem component 702. Instrument 800 includes a shaft portion 802 and a working end 804. The shaft portion 802 includes a handle 806 and a shaft neck 808 which may be smaller in diameter than the handle 806. The working end includes a distal facing surface 810 which is perpendicular to the longitudinal axis of the instrument. Projecting from the distal facing surface 810 are a first prong 812 and second prong 814. First prong 812 is sized and shaped to fit into any slot 762 of head component 704, proximal to arm 728, as seen in FIG. 7B. Second prong 812 is sized to fit into any bore 760 of head component 704. In the embodiment shown, second prong 814 is larger in diameter and longer than first prong 812, but the relative prong dimensions may vary in order to operatively engage with radial head trial 700 or other radial head trials.

In a method of use, instrument 800 is used to remove the trial head component 704 from the trial stem component in situ. Instrument 800 is engaged with trial head component, with first prong 812 inserted into a slot 762 with simultaneous insertion of second prong 814 into bore 760 adjacent slot 762. It is appreciated that instrument 800 can be inserted from any approach to trial head component 704; the first and second prongs 812, 814 will fit into any pair of adjacent slots 762 and bores 760 on the head component. When instrument 800 is fully inserted, distal facing surface 810 may contact head component 704 at peripheral wall 744. After instrument 800 is inserted into head component 704, instrument 800 may be actuated to pry or twist head component 704 from stem component 702. Handle 806 may be lifted, lowered, or moved transversely to pry, lever or twist the head component 704. During the removal process, first prong 812 may bear against arm 728 and/or slot 762 to force head component 704 proximally away from stem component 702. During the removal process, annular shoulder 766 may deflect and slots 762 may widen as spherical portion 726 is forced through annular shoulder 766. After trial head component 704 is removed, one or more additional trial head components may be snapped on to the stem component 702 to determine a properly sized and shaped prosthesis head. Once the desired prosthesis size is determined, trial stem component 702 may be removed from the resected radius, and a selected prosthesis may be implanted.

Any of the stem components disclosed herein may comprise ceramic, stainless steel, surgical steel or other suitable metals or alloys. The head components may comprise one or more materials, including but not limited to, polymers including acetal, polyphenylsulfone (PPSU), polyetherimide (PEI), polyether ether ketone (PEEK), polyethylene (PE) including high molecular weight grades; metals including stainless steel, cobalt-chrome or its alloys, or titanium and its alloys; ceramics; or any other articular bearing material. In an embodiment, the stem component 702 comprises metal and the head component 704 comprises a polymer, so that the relatively more elastic polymer head component can deflect as it is snapped on and off of the relatively more rigid metal stem component.

Some embodiments may include a stem component having a shaft that is curved, or a shaft that is multi-segmented, having 2 or more angled segments. The outer peripheral surface of the shaft may be generally rounded or cylindrical, or may be multi-faceted. In cross-section, the shaft may be circular, square, rectangular, triangular, hexagonal, star-shaped, or another cross-sectional shape. Any of the devices disclosed herein may include markings to indicate size, offset, and/or angulation.

The present invention may be embodied in other specific forms without departing from its spirit or essential characteristics. It is appreciated that various features of the above-described examples can be mixed and matched to form a variety of other alternatives. Trial head components, stem components, intermediate components and/or adjustment mechanisms may be interchangeable in any of the embodiments set forth herein, as may the orientation of the head component relative to the stem component. It is also contemplated that the embodiments disclosed herein may have application outside of the elbow joint; for example in wrist, shoulder, ankle, knee, or hip arthroplasty. As such, the described embodiments are to be considered in all respects only as illustrative and not restrictive.

The invention claimed is:

1. A radial head trial device for replacement of a proximal radial head, the device comprising:
    a stem component, the stem component including a center longitudinal axis extending between a proximal end and a distal end, the proximal end of the stem component including a boss structure, the boss structure including a spherical portion and a neck portion;
    a head component axially and removably attachable to the stem component, the head component including a proximal end having a concave surface formed therein, a distal end, and an outer bearing surface extending between the proximal and distal ends and defining a proximal to distal profile, the outer bearing surface including first and second convex portions, a first concave portion, and a third convex portion that form a contiguous series of arc segments such that the entire proximal to distal profile is either concavely or convexly curved, wherein the head component is radially symmetrical about a center longitudinal axis of the head component, and wherein the head component is interchangeable with a selection of other head components each axially and removably attachable to the stem component;
    an anti-rotation feature; and
    a recess formed in the head component, wherein the anti-rotation feature is structured to be received in the recess to prohibit rotation of the head component relative to the stem component.

2. The device of claim 1, wherein the recess of the head component includes a spherical recess portion structured to receive the spherical portion of the boss structure and an annular shoulder portion configured to receive the neck portion of the boss structure.

3. The device of claim 1, wherein the anti-rotation feature includes at least one arm extending from the stem component in a direction substantially orthogonal to the center longitudinal axis.

4. The device of claim 3, wherein the recess includes at least one slot configured to at least partially receive the at least one arm.

5. The device of claim 4, wherein the anti-rotation feature includes a plurality of arms equally spaced around a circumference of the stem component, and wherein the recess includes a corresponding plurality of slots.

6. The device of claim 1, wherein the head component includes at least one bore formed in an outer peripheral surface, the at least one bore structured to receive an engagement portion of a head removal instrument.

7. A radial head trial device for replacement of a proximal radial head, the device comprising:
    a stem component, the stem component including a shaft portion extending along a center longitudinal axis, a spherical boss portion, and a base ring including a plurality of anti-rotation arms extending therefrom;

a head component axially and removably attachable to the stem component along the center longitudinal axis, the head component including a spherical recess and an annular shoulder adjacent the spherical recess, the annular shoulder including a plurality of slots structured to receive the anti-rotation arms to minimize rotation of the head component relative to the stem component;

wherein the spherical boss portion is structured to be received in the spherical recess to attach the head component to the stem component; and wherein as the head component is pressed onto the stem component during attachment of the head and stem components, movement of the spherical boss portion through the annular shoulder is adapted to cause deflection of the annular shoulder by an amount sufficient to allow the spherical boss portion to be received within the spherical recess.

8. The device of claim 7, wherein the head component further includes a recessed ring that is shaped to receive the base ring.

9. The device of claim 7, wherein the stem component further includes a neck portion configured to be positioned within the annular shoulder when the spherical boss portion is received by the spherical recess.

10. The device of claim 7, wherein a proximal end of the head component includes a bearing surface defined by a concave portion surrounded by a circular rim.

11. The device of claim 7, wherein the stem component is formed from a metal and the head component is formed from a polymer.

12. The device of claim 7, wherein the head component includes a plurality of bores evenly spaced around an outer peripheral surface, each of the bores being configured for engagement with a connection feature on a head removal instrument.

13. A radial head trial device comprising:

a stem component, the stem component including a shaft portion extending along a center longitudinal axis and a stem attachment portion, the stem attachment portion including a spherical boss portion and a plurality of anti-rotation arms extending from the stem component in a direction substantially orthogonal to the center longitudinal axis; and a head component axially and removably attachable to the stem component along the center longitudinal axis, the head component including a proximal end having a concave surface formed therein, a distal end, and an outer bearing surface extending between the proximal and distal ends, the head component further including a spherical recess, an annular shoulder adjacent the spherical recess, and a plurality of slots extending from the distal end of the head component through the annular shoulder, the slots configured to allow deflection of the annular shoulder during attachment of the head component to the stem component;

wherein the spherical boss portion is structured to be received in the spherical recess to attach the head component to the stem component; and wherein the anti-rotation arms are structured to be received in the slots to substantially prevent rotation of the head component relative to the stem component.

* * * * *